(12) United States Patent
Szucs

(10) Patent No.: US 6,413,913 B1
(45) Date of Patent: Jul. 2, 2002

(54) THIONO-THIOCHROMAN AND -DIHYDROBENZOTHIOPHENE COMPOUNDS AS HERBICIDAL AGENTS

(75) Inventor: Stephen S. Szucs, Lawrenceville, NJ (US)

(73) Assignees: BASF Corporation, Mount Olive, NJ (US); Idemitsu Kosen Company, Ltd., Tokyo (JP)

( * ) Notice: Subject to any disclaimer, the term of this patent is extended or adjusted under 35 U.S.C. 154(b) by 0 days.

(21) Appl. No.: 09/693,448

(22) Filed: Oct. 20, 2000

Related U.S. Application Data

(60) Provisional application No. 60/161,241, filed on Oct. 22, 1999.

(51) Int. Cl.[7] .................... C07D 407/10; C07D 409/10; A01N 43/56
(52) U.S. Cl. ..................... 504/282; 548/364.4
(58) Field of Search ........................ 548/364.4; 504/282

(56) References Cited

U.S. PATENT DOCUMENTS 5,468,722 A   11/1995   Shibata et al. .............. 504/282
5,607,898 A   3/1997    Nakamura et al. ........... 504/282

FOREIGN PATENT DOCUMENTS

EP   0 629 623 A1   12/1994
WO   WO 97/08164    3/1997   ......... C07D/335/06

Primary Examiner—Mark Berch
Assistant Examiner—Kahsay Habte
(74) Attorney, Agent, or Firm—Charles F. Costello

(57) ABSTRACT

The present invention provides a compound of formula I:

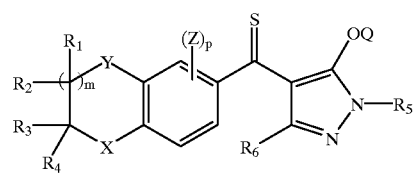

wherein X is O or $S(O)_n$; n is zero, 1 or 2; and Y is $CR_7R_8$, $CHOR_9$, $C(OR_9)_2$, $C=NOR_{10}$ or $C=NNR_{20}R_{21}$.

Compounds of formula I are useful as herbicidal agents, particularly as agents for the control of undesirable plant species in the presence of a cereal crop.

20 Claims, No Drawings

THIONO-THIOCHROMAN AND -DIHYDROBENZOTHIOPHENE COMPOUNDS AS HERBICIDAL AGENTS

This application claims priority from provisional application Ser. No. 60/161,154 filed Oct. 22, 1999.

BACKGROUND OF THE INVENTION

Weeds cause tremendous global economic losses by reducing crop yields and lower crop quality. Worldwide agronomic crops must compete with hundreds of weed species. Herbicides, used to combat these weed species are now standard technology on farms and ranches. The proper agronomic use of herbicides results in increased crop yields and quality and, concomitantly, increases production and harvesting efficiency.

In spite of the commercial herbicides available, damage to crops caused by weeds still occurs. In addition, often herbicides do not provide a sufficient margin of safety for the crop, thus damaging the crop as well as the weeds. Accordingly, there is an ongoing need to create more crop-selective as well as more effective herbicidal agents.

Thiochroman and dihydrobenzothiophene (DHBT) herbicidal agents are described in U.S. Pat. No. 5,607,898 and WO 97/08164. However, none of the compounds described therein contain a thiono moiety.

It is therefore an object of the present invention to provide thiono-thiochroman and thiono-dihydrobenzothiophene compounds which demonstrate herbicidal activity in conjunction with crop safety.

SUMMARY OF THE INVENTION

The present invention provides a herbicidal compound of formula I

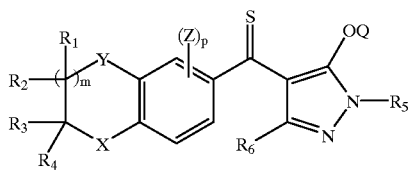

(I)

wherein m is zero or 1;

$R_1$, $R_2$, $R_3$ and $R_4$ are each, independently, H, $C_1$–$C_4$ alkyl, $C_1$–$C_4$ haloalkyl or $C_2$–$C_4$ alkoxyalkyl;

$R_5$ is $C_1$–$C_3$ alkyl, $C_2$–$C_4$ alkenyl, or $C_2$–$C_4$ haloalkyl;

$R_6$ is H, halogen, CN, $NO_2$, $C_1$–$C_4$ alkyl, $C_2$–$C_4$ alkenyl, or $C_2$–$C_4$ alkoxyalkyl.

X is O or $S(O)_n$;

n is zero, 1 or 2;

Y is $CR_7R_8$, $CHOR_9$, $C(OR_9)_2$, $C=NOR_{10}$, C=O or $C=NNR_{20}R_{21}$;

$R_7$ is H, $C_1$–$C_4$ alkyl or $C_1$–$C_4$ haloalkyl;

$R_8$ is H, $C_1$–$C_4$ alkyl or $C_2$–$C_4$ alkenyl or $C_2$–$C_4$ alkenyl;

$R_9$ and $R_{10}$ are each, independently H, $C_1$–$C_6$ alkyl optionally substituted with one or more halogen, $C_1$–$C_4$ alkoxy, $C_2$–$C_6$ alkenyl, $C_2$–$C_6$ alkynyl, $C_1$–$C_6$ haloalkyl or $C_3$–$C_6$ cycloalkyl groups, or when two $R_9$ groups are present they may be taken together with the atoms to which they are attached to form a five- or six-membered ring;

Q is H, $SO_2R_{11}$, $COR_{12}$, $CO_2R_{13}$, $P(O)(OR_{14})_2$ or $C_1$–$C_4$ alkyl optionally substituted with $COR_{15}$, $CO_2R_{16}$, P(O) $(OR_{17})_2$ or phenyl optionally substituted with one to three halogen, $NO_2$, $C_1$–$C_4$ alkyl, $C_1$–$C_4$ alkoxy or $C_1$–$C_4$ haloalkyl groups;

$R_{11}$, $R_{13}$, $R_{14}$, and $R_{17}$ are each independently $C_1$–$C_8$ alkyl, $C_3$–$C_8$ cycloalkyl, or phenyl, optionally substituted with one to three halogen, nitro, $C_1$–$C_4$ alkyl, $C_1$–$C_4$ alkoxy or $C_1$–$C_4$ haloalkyl groups;

$R_{12}$ and $R_{15}$ are each independently H, $NR_{18}R_{19}$, $C_1$–$C_8$ alkyl, $C_3$–$C_8$ cycloalkyl or phenyl optionally substituted with one to three halogen, $NO_2$, $C_1$–$C_4$ alkyl, $C_1$–$C_4$ alkoxy or $C_1$–$C_4$ haloalkyl groups;

$R_{16}$ is H, $C_1$–$C_8$ alkyl, $C_3$–$C_8$ cycloalkyl or phenyl optionally substituted with one to three halogen, $NO_2$, $C_1$–$C_4$ alkyl, $C_1$–$C_4$ alkoxy or $C_1$–$C_4$ haloalkyl groups;

$R_{18}$ and $R_{19}$ are each independently H or $C_1$–$C_6$ alkyl;

$R_{20}$ and $R_{21}$ are each independently H or $C_1$–$C_6$ alkyl or $R_{20}$ and $R_{21}$ may be taken together with the atom to which they are attached to form a five- or six-membered ring;

Z is H, halogen, $C_1$–$C_4$ alkyl, $C_1$–$C_4$ haloalkyl, $C_2$–$C_4$ alkoxyalkyl, $C_1$–$C_4$ alkoxy or $C_1$–$C_4$ haloalkoxy; and p is zero, 1, 2, or 3; or the agriculturally acceptable salts thereof.

Also provided are herbicidal compositions and methods and a process for the preparation of the Formula I compound.

DETAILED DESCRIPTION OF THE INVENTION

The term safety or selectivity in weed science refers to the characteristic by which undesirable species of plants (weeds) are killed or seriously injured in the presence of desirable plant species (crops) without concomitant injury of the desired plant species. The use of herbicides frequently causes a varying degree of crop injury. Such crop damage is a problem that generates a continuous need for more selective herbicides worldwide. This is especially true of crops such as cereals which are often unacceptably damaged by herbicides designed to protect said crops against invasive weeds.

Surprisingly, it has now been found that the formula I compounds of the invention demonstrate good herbicidal efficacy against undesirable plant species along with enhanced crop selectivity. In particular, the formula I compounds of this invention are surprisingly safe in cereal crops such as corn, wheat, rice, or the like, preferably corn.

Compounds of the invention have the structural formula I

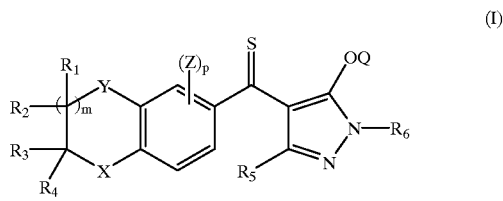

(I)

wherein $R_1$, $R_2$, $R_3$, $R_4$, $R_5$, $R_6$, Q, X, Y, Z, m and p are described hereinabove.

The term halogen as used in the specification and claims designates chlorine, fluorine, bromine or iodine. The term haloalkyl designates an alkyl group, $C_nH_{2n+1}$ which may contain from one halogen atom to 2n+1 halogen atoms. Similarly, the term haloalkoxy designates a $OC_nH_{2n+1}$ group which may contain from one to 2n+1 halogen atoms.

Haloalkenyl designates an alkenyl group $C_nH_{2n}$ which may contain from one to 2n halogen atoms. In each instance the halogen atoms may be the same or different.

The formula I compounds of the invention include all stereoisomeric and regioisomeric embodiments.

The agriculturally acceptable salts of formula I include salts such as alkali metal, e.g. lithium, sodium or potassium; alkaline-earth metal, e.g. calcium or magnesium; ammonium or amine, e.g. diethanolamine, triethanolamine, octylamine, morpholine, dioctylmethylamine or any of the conventional salts suitable for use in standard agricultural practice.

Preferred compounds of the present invention are those formula I compounds wherein X is $SO_2$; Q is H; and Y is $CR_7R_8$, $CHOR_9$, $C(OR_9)_2$ or $C=NOR_{10}$.

Compounds of formula I, wherein Q is hydrogen, may be prepared from the corresponding ketone by treatment of said ketone with Lawesson's Reagent in the presence of a solvent, preferably an inert solvent such as dimethoxyethane. The reaction is shown below in Flow Diagram I.

Flow Diagram I

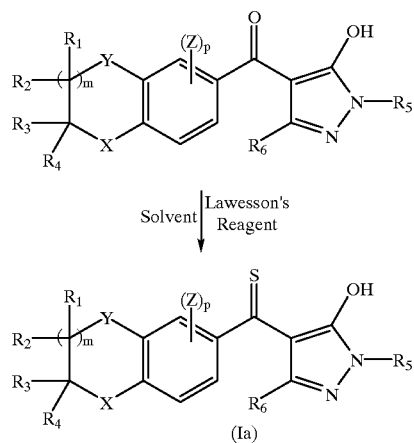

Lawesson's reagent may be represented by the structure shown below and is available commercially.

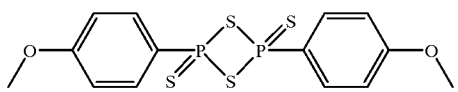

Compounds of formula I in which Q is $SO_2R_{11}$ may be prepared by treating the formula I compound wherein Q is hydrogen with a suitable sulfonating agent, $R_{11}SO_2$halide, in the presence of a base, preferably potassium carbonate. The reaction may be conveniently carried out in a two-phase solvent system in the presence of a phase-transfer catalyst such as benzyltriethylammonium chloride (BTEAC). The reaction is shown in Flow Diagram II, wherein the sulfonyl halide is a sulfonyl chloride.

Flow Diagram II

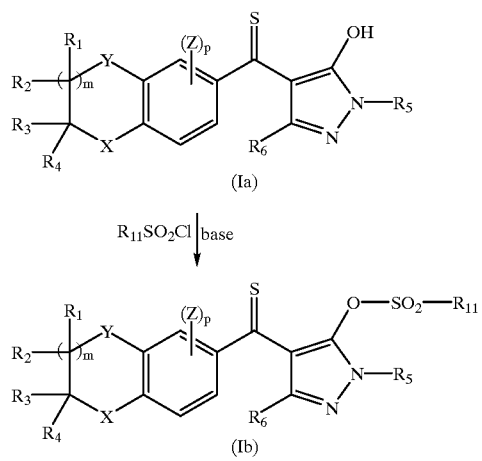

Compounds of formula I wherein Q is is other than H or $SO_2R_{11}$ may be prepared in a manner similar to that described in U.S. Pat. No. 5,607,898 or in WO 97/08164.

Advantageously, it has now been found that the formula I compounds of the invention are particularly useful for the selective control of undesirable plant species in the presence of crop plants, seeds or other propagating organs. In particular, the compounds of this invention are selective in cereal crops such as corn, wheat, rice or the like, preferably corn.

In actual practice, the compounds of the invention may be applied to the foliage of undesirable plants or to the soil or water containing seeds or other propagating organs thereof, preferably to the foliage, in the form of a solid or liquid herbicidal composition. Said composition may take the form of an emulsifiable concentrate, a concentrated emulsion, a wettable powder, a soluble granule, a suspension concentrate, a flowable concentrate or any convenient conventional form useful for herbicide application.

The composition of the invention comprises an agronomically acceptable inert solid or liquid carrier and a herbicidally effective amount of a compound of formula I. The herbicidally effective amount of the formula I compound may vary according to the prevailing conditions such as weed pressure, crop species, application timing, form of application, soil conditions, weather conditions or the like. In general, hebicidally effective amounts may be obtained when the composition of the invention is applied at rates of about 0.001 kg/ha to 10.0 kg/ha, preferably about 0.003 to 0.50 kg/ha, more preferably about 0.006 to 0.20 kg/ha.

The composition of the invention may be applied in combination with other herbicides such as dinitroanilines, for example trifluralin, pendimethalin or the like, preferably pendimethalin; triazines, for example atrazine, cyanazine, metribuzin or the like; AHAS inhibitors for example imidazolinones, sulfonyl ureas or the like; protox inhibitors; or any of the commonly employed, commercially available herbicidal agents. Said combination may be applied sequentially or concurrently as a tank-mix or co-formulation. Compositions of the invention embrace compounds of formula I alone or in combination with a second herbicide as active ingredient, preferably pendimethalin.

In order to further illustrate the invention, the following examples are set forth below. The terms $^1$HNMR, $^{13}$CNMR designate proton and carbon NMR, respectively and the terms IR and MS designate infrared spectrometry and mass spectroscopy, respectively. The terms HPLC and TLC designate high performance liquid chromatography and thin layer chromatography, respectively. Unless otherwise stated, all parts are parts by weight.

EXAMPLE 1

Preparation of 6-[(1-Ethyl-5-hydroxypyrazol-4-yl)thicarbonyl]-5-methylthiochroman-4-one (E) -O-Methyloxime, 1,1-Dioxide

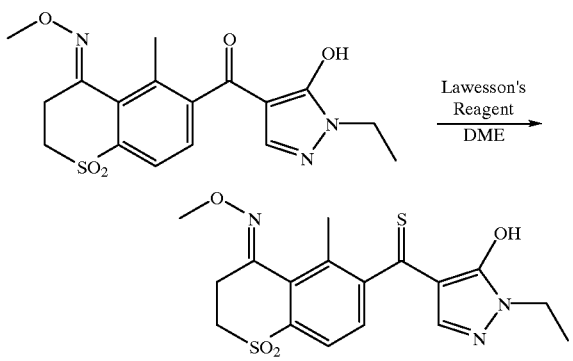

A stirred suspension of the 4-(O-methyloxime) of 6-[(1-ethyl-5-hydroxypyrazol-4-yl)carbonyl]-5-methyl-thiochroman-4-one 1,1-dioxide (50.0 g, 0.132 mol) in 500 mL dimethoxyethane (DME), under nitrogen, is treated with Lawesson's Reagent (53.6 g, 0.132 mol), heated at 65–70° or a period of 15 h [during this period, additional Lawesson's Reagent is added (39.5 g, 0.098 mol)], cooled to room temperature and filtered. The filtrate is concentrated in vacuo to give a syrup. The syrup is diluted with diethyl ether, washed sequentially with water and brine, dried over sodium sulfate and concentrated in vacuo to give a second syrup. The second syrup is dissolved in methylene chloride and chromatographed on silica gel using a gradient elution ($CH_2Cl_2/Et_2O$: 100/0 to 90/10) to give the title compound as a golden-yellow solid, mp 92°–97° C., 24.1 g, (46.1% yield), identified by IR, $^1HNMR$, $^{13}CNMR$ and MS analyses. Quantitative NMR analysis indicates a product purity of 97.7% with the ratio of oxime isomers (E/Z: 95/5) unchanged

EXAMPLES 2–4

Preparation of Thiono-thiochroman and -Dihydrobenzo [b] thiohene Compounds

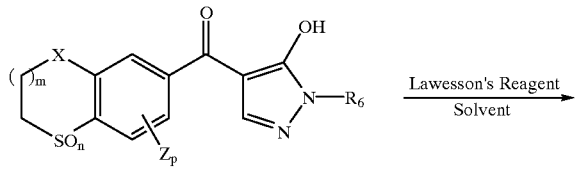

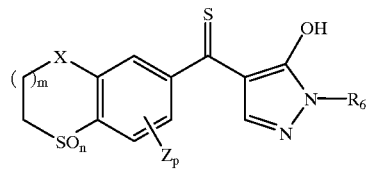

Using essentially the same procedure described in Example 1 (and employing the appropriate keto substrate, the compounds shown in Table I are obtained.

TABLE I

| Ex. No. | $R_6$ | $R_7$ | $R_8$ | $Z_p$ | m | n | mp ° C. |
|---|---|---|---|---|---|---|---|
| 2 | $C_2H_5$ | $CH_3$ | $CH_3$ | 5,8-di-$CH_3$ | 1 | 2 | — |
| 3 | $CH_3$ | $CH_3$ | $CH_3$ | 4-$CH_3$ | 0 | 2 | 214–216 |
| 4 | $C_2H_5$ | $CH_3$ | $CH_3$ | 4-$CH_3$ | 0 | 2 | 136–134 |

EXAMPLE 5

Preparation of 6-{[1-Ethyl-5-sulfonyloxy)pyrazol-4-yl]thiocarbonyl}-5-methylthiochroman-4-one (E)-O-Methyloxime, 1,1-Dioxide

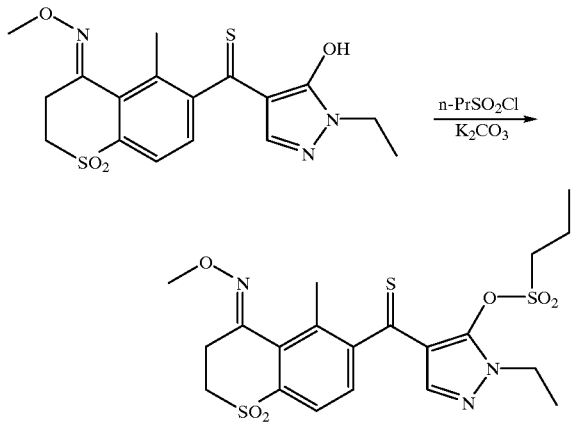

A solution of 6-[(1-ethyl-5-hydroxypyrazol-4-yl)thiocarbonyl]-5-methylthiochroman-4-one (E)-O-methyloxime, 1,1-dioxide (0.81 g, 2.1 mmol) in methylene chloride is treated with 0.34 g potassium carbonate, 0.024 g benzyltriethylammonium chloride, water and n-propylsulfonyl chloride (0.44 g, 3.1 mmol), stirred at room temperature for 18 hr and diluted with methylene chloride and water. The phases are separated and the aqueous phase is washed sequentially with methylene chloride. The combined organic phases are washed with water, 1% HCl, water, and brine, dried over anhydrous magnesium sulfate and concentrated in vacuo to give a dark brown syrup. The syrup is purified by silica gel chromatography, using gradient elution (methylene chloride/ether: 100/0–95/5) to give the title product as a yellow-brown solid, mp 95–105° C., (54% yield) characterized by $^{13}$CNMR, $^1$HNMR and mass spectral analyses.

EXAMPLE 6

Postemergence Herbicidal Evaluation Of Test Compounds

The herbicidal activity of the compounds of the present invention is evaluated by the following tests Seedling plants are grown in jiffy flats for about two weeks. The test compounds are dispersed in 80/20 (v/v) acetone/water mixtures containing 1.0% SUN-IT® II, a methylated seed oil, in sufficient quantities to provide the equivalent of about 0.006 kg/ha to 0.800 kg/ha of active compound when applied to the plants through a spray nozzle operating at 40 psi for a predetermined time. After spraying, the plants are placed on greenhouse benches and are cared for in accordance with conventional greenhouse procedures. Approximately two—three weeks after treatment, the seedling plants are examined and rated according to the rating system set forth below. Where more than one test is involved for a given compound, the data are averaged. The results are shown in Table II.

HERBICIDE RATING SCALE

| Rating | % Control as compared to the untreated check |
|---|---|
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | 0 |

PLANT SPECIES EMPLOYED

| Header Abbr. | Common Name | Scientific Name |
|---|---|---|
| ABUTH | Velvetleaf | *Abutilon theophrasti*, Medic. |
| AMBEL | Ragweed, Common | *Ambrosia artemisifolia*, L. |
| CASOB | Sicklepod | *Cassia Obtusifolia*, L. |
| CHEAL | Lambsquarters, | *Chenopodium album*, L. Common |
| IPOSS | Morningglory, spp. | *Ipomoea* spp. |
| IPOHE | Morningglory, Ivyleaf | *Ipomoea hederacea*, (L) Jacq. |
| ECHCG | Barnyardgrass | *Echinochloa crus-galli*, (L.) Beau |
| PANDI | Panicum, Fall | *Panicum dichotomiflorum*, Michx. |
| SETVI | Foxtail, Green | *Setaria viridis*, (L.) Beau |
| ZEAMX | Corn, Field | *Zea mays*, L. |

TABLE II

POSTEMERGENCE HERBICIDAL EVALUATION

| Example Number | Rate (kg/ha) | ABUTH | AMBEL | IPOHE | ECHCG | PANDI | SETVI | ZEAMX |
|---|---|---|---|---|---|---|---|---|
| 1 | 0.100 | 8.0 | 8.4 | 3.0 | 7.8 | 6.5 | 9.0 | 3.0 |
|   | 0.050 | 7.6 | 8.2 | 2.0 | 8.0 | 6.3 | 8.5 | 1.2 |
| 2 | 0.100 | 9.0 | 9.0 | 4.0 | 9.0 | 4.0 | 9.0 | 1.0 |
|   | 0.050 | 9.0 | 6.0 | 2.0 | 5.0 | 5.0 | 9.0 | 0.0 |
| 3 | 0.100 | 8.0 | 8.0 |     | 9.0 | 8.0 | 8.0 | 3.0 |
|   | 0.050 | 9.0 | 9.0 |     | 7.0 | 7.0 | 8.0 | 2.0 |
| 4 | 0.100 | 7.0 | 8.0 | 4.0 | 8.0 | 9.0 | 7.0 | 2.0 |
|   | 0.050 | 4.0 | 8.0 | 4.0 | 8.0 | 3.0 | 4.0 | 0.0 |
| 5 | 0.100 |     |     |     |     |     |     | 3.0 |
|   | 0.050 |     |     |     |     |     |     | 0.0 |

EXAMPLE 7

Preemergence Herbicidal Evaluation of Test Compounds

In these tests, seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.0125 to 0.800 kg per hectare of test compound per cup. The treated cups are then placed on greenhouse benches, watered and cared for in accordance with conventional greenhouse procedures. Approximately two—four weeks after treatment, the tests are terminated and each cup is examined and rated according to the rating system provided in Example 6. The results obtained are shown in Table III.

TABLE III

PREEMERGENCE HERBICIDAL EVALUATION

| Example Number | Rate (kg/ha) | ABUTH | AMBEL | IPOHE | ECHCG | PANDI | SETVI | ZEAMX |
|---|---|---|---|---|---|---|---|---|
| 1 | 0.100 | 9.0 | 8.8 | 6.0 | 8.3 | 8.5 | 8.4 | 0.8 |
|   | 0.050 | 7.3 | 8.5 | 2.5 | 5.8 | 8.0 | 6.6 | 0.0 |
| 2 | 0.100 | 9.0 | 3.0 | 0.0 | 3.0 | 7.0 | 5.0 | 0.0 |
|   | 0.050 | 3.0 | 2.0 | 0.0 | 0.0 | 5.0 | 4.0 | 0.0 |
| 3 | 0.100 | 9.0 | 7.0 | 2.0 | 8.5 | 8.0 | 7.0 | 0.0 |
|   | 0.050 | 8.0 | 5.5 | 2.0 | 7.0 | 6.5 | 5.0 | 0.0 |
| 4 | 0.100 | 9.0 | 9.0 | 1.0 | 9.0 | 7.0 | 3.0 | 0.0 |
|   | 0.050 | 6.0 | 2.0 | 1.0 | 2.0 | 2.0 | 3.0 | 0.0 |
| 5 | 0.100 | 9.0 | 9.0 |     | 6.0 | 7.0 | 6.0 | 0.0 |
|   | 0.050 | 9.0 | 7.0 |     | 6.0 | 7.0 | 6.0 | 0.0 |

I claim:

1. A compound of formula I

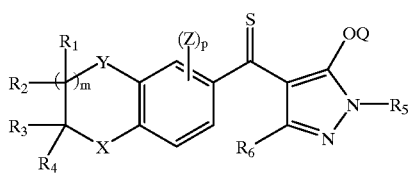

wherein m is zero or 1;

$R_1$, $R_2$, $R_3$ and $R_4$ are each independently, H, $C_1$–$C_4$ alkyl, $C_1$–$C_4$ haloalkyl or $C_2$–$C_4$ alkoxyalkyl;

$R_5$ is $C_1$–$C_3$ alkyl, $C_2$–$C_4$ alkenyl, or $C_2$–$C_4$ haloalkyl;

$R_6$ is H, halogen, CN, $NO_2$, $C_1$–$C_4$ alkyl, $C_2$–$C_4$ alkenyl, or $C_2$–$C_4$ alkoxyalkyl;

X is O or $S(O)_n$;

n is zero, 1 or 2;

Y is $CR_7R_8$, $CHOR_9$, $C(OR_9)_2$, $C=NOR_{10}$ or $C=NNR_{20}R_{21}$;

$R_7$ is H, $C_1$–$C_4$ alkyl or $C_1$–$C_4$ haloalkyl;

$R_8$ is H, $C_1$–$C_4$ alkyl or $C_2$–$C_4$ alkenyl or $C_2$–$C_4$ alkynyl;

$R_9$ and $R_{10}$ are each, independently H or $C_1$–$C_6$ alkyl optionally substituted with one or more halogen, $C_1$–$C_4$ alkoxy, $C_2$–$C_6$ alkenyl, $C_2$–$C_6$ alkynyl, $C_1$–$C_6$ haloalkyl or $C_3$–$C_6$ cycloalkyl groups;

Q is H, $SO_2R_{11}$, $COR_{12}$, $CO_2R_{13}$, $P(O)(OR_{14})_2$ or $C_1$–$C_4$ alkyl optionally substitute $COR_{15}$, $CO_2R_{16}$, $P(O)(OR_{17})_2$ or phenyl optionally substituted with one to three halogen, $NO_2$, $C_1$–$C_4$ alkyl, $C_1$–$C_4$ alkoxy or $C_1$–$C_4$ haloalkyl groups;

$R_{11}$, $R_{13}$, $R_{14}$, and $R_{17}$ are each independently $C_1$–$C_8$ alkyl, $C_3$–$C_8$ cycloalkyl, or phenyl, optionally substituted with one to three halogen, nitro, $C_1$–$C_4$ alkyl, $C_1$–$C_4$ alkoxy or $C_1$–$C_4$ haloalkyl groups;

$R_{12}$ and $R_{15}$ are each independently H, $NR_{18}R_{19}$, $C_1$–$C_8$ alkyl, $C_3$–$C_8$ cycloalkyl or phenyl optionally substituted with one to three halogen, $NO_2$, $C_1$–$C_4$ alkyl, $C_1$–$C_4$ alkoxy or $C_1$–$C_4$ haloalkyl groups;

$R_{16}$ is H, $C_1$–$C_8$ alkyl, $C_3$–$C_8$ cycloalkyl or phenyl optionally substituted with one to three halogen, $NO_2$, $C_1$–$C_4$ alkyl, $C_1$–$C_4$ alkoxy or $C_1$–$C_4$ haloalkyl groups;

$R_{18}$ to $R_{21}$ are each independently H or $C_1$–$C_6$ alkyl;

Z is H, halogen, $C_1$–$C_4$ alkyl, $C_1$–$C_4$ haloalkyl, $C_2$–$C_4$ alkoxyalkyl, $C_1$–$C_4$ alkoxy or $C_1$–$C_4$ haloalkoxy; and p is zero, 1,2, or 3; or the agriculturally acceptable salts thereof.

2. The compound according to claim 1 wherein X is $SO_2$; Q is H; and Y is $CR_7R_8$, $CHOR_9$, $C(OR_9)_2$, or $C=NOR_{10}$.

3. The compound according to claim 2 wherein $R_7$ and $R_8$ are each independently $C_1$–$C_4$ alkyl.

4. The compound according to claim 2 wherein $R_{10}$ is $C_1$–$C_4$ alkyl.

5. The compound according to claim 4 6-[(1-ethyl-5-hydroxypyrazol-4-yl)thiocarbonyl]-5-methylthiochroman-4-one-O-methyloxime, 1,1-dioxide.

6. A method for the control of undesirable plants which comprises applying to the foliage of said plants or to the soil or water containing seeds or other propagating organs thereof a herbicidally effective amount of a compound of formula I

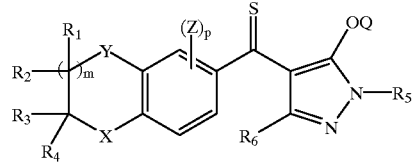

wherein $R_1$, $R_2$, $R_3$, $R_4$, $R_5$, $R_6$, Q. X, Y, Z, m and p are as described in claim 1.

7. The method according to claim 6 wherein the formula I compound is applied to the foliage of said plants.

8. The method according to claim 6 wherein said undesirable plants are in the presence of a crop.

9. The method according to claim 8 wherein said crop is a cereal crop.

10. The method according to claim 9 wherein said crop is corn.

11. The method according to claim 6 having a formula I compound wherein X is $SO_2$; Q is H; and Y is $CR_7R_8$, $CHOR_9$, $C(OR_9)_2$, or $C=NOR_{10}$.

12. The method according to claim 11 wherein $R_7$ and $R_8$ are each independently $C_1$–$C_4$ alkyl.

13. The method according to claim 11 wherein $R_{10}$ is $C_1$–$C_4$ alkyl.

14. The method according to claim 13 wherein the formula I compound is 6-[(1-ethyl-5-hydroxypyrazol-4-yl)thiocarbonyl]-5-methylthiochroman-4-one, O-methyloxime, 1,1-dioxide.

15. The method according to claim 6 wherein the formula I compound is applied at a rate of about 0.001 kg/ha to 10.0 kg/ha.

16. The method according to claim 15 wherein the formula I compound is applied at a rate of about 0.006 kg/ha to 1.0 kg/ha.

17. A herbicidal composition which comprises an agriculturally acceptable carrier and a herbicidally effective amount of a compound of formula I

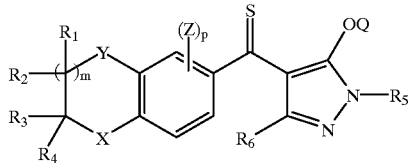

(I)

wherein $R_1$, $R_2$, $R_3$, $R_4$, $R_5$, $R_6$, Q, X, Y, Z, m and p are as described in claim 1.

18. The composition according to claim 17 having a formula I compound wherein X is $SO_2$; Q is H; and Y is $CR_7R_8$, $CHOR_9$, $C(OR_9)_2$, or $C=NOR_{10}$.

19. The composition according to claim 18 wherein $R_{10}$ is $C_1$–$C_4$ alkyl.

20. A process for the preparation of a compound of formula Ia

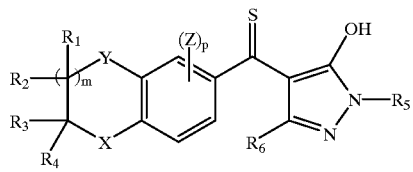

(Ia)

wherein m is zero or 1;

$R_1$, $R_2$, $R_3$ and $R_4$ are each, independently, H, $C_1$–$C_4$ alkyl, $C_1$–$C_4$ haloalkyl or $C_2$–$C_4$ alkoxyalkyl;

$R_5$ is $C_1$–$C_3$ alkyl, $C_2$–$C_4$ alkenyl, or $C_2$–$C_4$ haloalkyl;

$R_6$ is H, halogen, CN, $NO_2$, $C_1$–$C_4$ alkyl, $C_2$–$C_4$ alkenyl, or $C_2$–$C_4$ alkoxyalkyl;

X is O or $S(O)_n$ n is zero, 1 or 2;

Y is $CR_7R_8$, $CHOR_9$, $C(OR_9)_2$, $C=NOR_{10}$ or $C=NNR_{20}R_{21}$;

$R_7$ is H, $C_1$–$C_4$ alkyl or $C_1$–$C_4$ haloalkyl;

$R_8$ is H, $C_1$–$C_4$ alkyl or $C_2$–$C_4$ alkenyl or $C_2$–$C_4$ alkynyl;

$R_9$ and $R_{10}$ are each, independently H or $C_1$–$C_6$ alkyl optionally substituted with one or more halogen, $C_1$–$C_4$ alkoxy, $C_2$–$C_6$ alkenyl, $C_2$–$C_6$ alkynyl, $C_1$–$C_6$ haloalkyl or $C_3$–$C_6$ cycloalkyl groups;

$R_{20}$ and $R_{21}$ are each independently H or $C_1$–$C_6$ alkyl;

Z is H, halogen, $C_1$–$C_4$ alkyl, $C_1$–$C_4$ haloalkyl, $C_2$–$C_4$ alkoxyalkyl, $C_1$–$C_4$ alkoxy or $C_1$–$C_4$ haloalkoxy; and p is zero, 1, 2, or 3 which process comprises reacting a compound of formula II

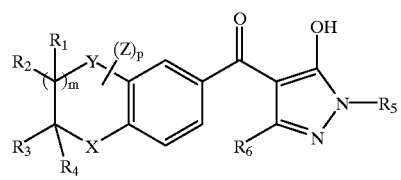

II with Lawesson's Reagent in the presence of a solvent.

* * * * *

UNITED STATES PATENT AND TRADEMARK OFFICE
CERTIFICATE OF CORRECTION

PATENT NO.    : 6,413,913 B1
DATED         : July 2, 2002
INVENTOR(S)   : Szucs et al.

It is certified that error appears in the above-identified patent and that said Letters Patent is hereby corrected as shown below:

Column 9,
Line 49, "substitute" should be -- substituted with --.

Signed and Sealed this

Fifteenth Day of October, 2002

*Attest:*

*Attesting Officer*

JAMES E. ROGAN
*Director of the United States Patent and Trademark Office*